(12) United States Patent
Sugita

(10) Patent No.: US 11,583,167 B2
(45) Date of Patent: Feb. 21, 2023

(54) ENDOSCOPE HOOD REMOVAL TOOL AND SET OF HOOD AND HOOD REMOVAL TOOL

(71) Applicant: HOYA CORPORATION, Tokyo (JP)

(72) Inventor: Noriyuki Sugita, Tokyo (JP)

(73) Assignee: HOYA CORPORATION, Tokyo (JP)

(*) Notice: Subject to any disclaimer, the term of this patent is extended or adjusted under 35 U.S.C. 154(b) by 329 days.

(21) Appl. No.: 16/642,607

(22) PCT Filed: Nov. 2, 2018

(86) PCT No.: PCT/JP2018/040856
§ 371 (c)(1),
(2) Date: Feb. 27, 2020

(87) PCT Pub. No.: WO2019/093240
PCT Pub. Date: May 16, 2019

(65) Prior Publication Data
US 2020/0187757 A1    Jun. 18, 2020

(30) Foreign Application Priority Data
Nov. 13, 2017 (JP) .............................. JP2017-218462

(51) Int. Cl.
*A61B 1/00*    (2006.01)
*A61B 1/31*    (2006.01)

(52) U.S. Cl.
CPC ...... *A61B 1/00101* (2013.01); *A61B 1/00089* (2013.01); *A61B 1/00131* (2013.01); *A61B 1/31* (2013.01)

(58) Field of Classification Search
CPC ............ A61B 1/00089; A61B 1/00101; A61B 1/00131; A61B 1/00135; A61B 1/00057;
(Continued)

(56) References Cited

U.S. PATENT DOCUMENTS 5,820,547 A * 10/1998 Strobl ................ A61B 1/00163
600/117
D860,442 S    9/2019 Ostrovsky et al.
(Continued)

FOREIGN PATENT DOCUMENTS

JP    10-127578    5/1998
JP    H10127578 A * 5/1998 ............... A61B 1/00
(Continued)

OTHER PUBLICATIONS

International Search Report issued in International Patent Application No. PCT/JP2018/040856, dated Jan. 29, 2019.

*Primary Examiner* — Aaron B Fairchild
(74) *Attorney, Agent, or Firm* — Greenblum & Bernstein, P.L.C.

(57) ABSTRACT

A removal tool for removing a hood having a hollow cylindrical shape mounted to a distal tip of an endoscope from the distal tip is constituted from a flexible member including a hole-shaped recess capable of housing the hood in its inside. An outer surface of the hood is provided with a step portion that extends along a circumferential direction of the hood. An inner wall surface of the recess is provided with an engaging portion at a position opposing to the step portion when the hood is housed in the recess, the engaging portion being shaped to grip the hood by being engaged with the step portion as a result of deformation of the flexible member.

13 Claims, 9 Drawing Sheets

(58) Field of Classification Search
CPC .............. A61B 1/0008; A61B 1/00096; A61B 1/00097
See application file for complete search history.

(56) References Cited

U.S. PATENT DOCUMENTS

| | | | | |
|---|---|---|---|---|
| 2003/0088155 A1* | 5/2003 | Ishibiki | .............. | A61B 1/00089 600/127 |
| 2004/0077928 A1* | 4/2004 | Moriyama | ......... | A61B 1/00089 600/127 |
| 2018/0289245 A1 | 10/2018 | Yamaya | | |
| 2019/0142242 A1* | 5/2019 | Yamaya | ................ | G02B 23/24 600/101 |

FOREIGN PATENT DOCUMENTS

| | | |
|---|---|---|
| JP | 5404258 | 1/2014 |
| JP | 1605825 S | 6/2018 |
| WO | 2017/122559 | 7/2017 |

\* cited by examiner

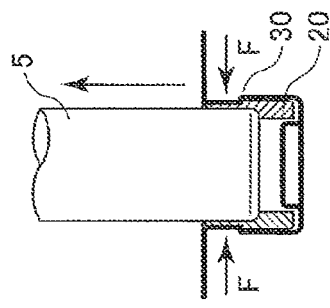
FIG. 7 (d)
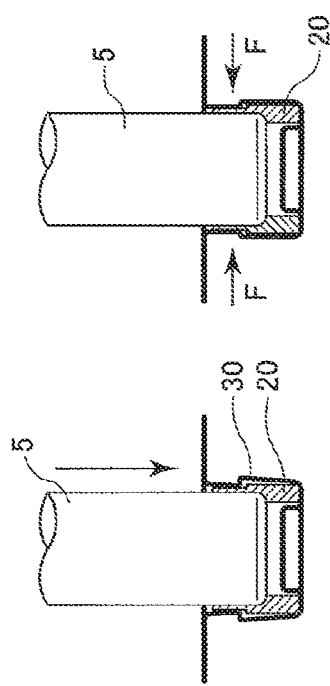
FIG. 7 (c)
FIG. 7 (b)
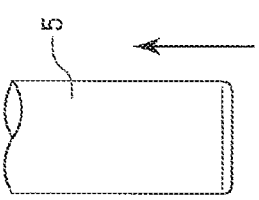
FIG. 7 (e)
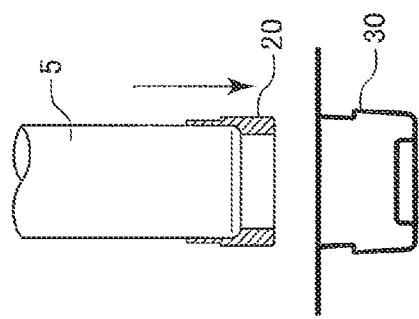
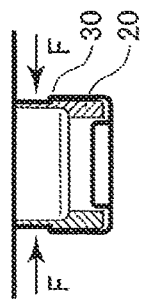
FIG. 7 (a)

ENDOSCOPE HOOD REMOVAL TOOL AND SET OF HOOD AND HOOD REMOVAL TOOL

TECHNICAL FIELD

The present invention relates to a removal tool of a hood mounted to a distal tip of an endoscope, and a set of the hood and the hood removal tool.

BACKGROUND ART

A distal tip of an insertion portion of an endoscope is provided with an opening for acquiring an image of a biotissue and an outlet of illumination light for illuminating the biotissue, and a hood is mounted to the distal tip to prevent the opening and the outlet from becoming dirty with an adhered substance. The hood is a tubular member having a hollow cylindrical shape formed from a resin material. Various treatment devices such as biological forceps, a cell collection brush, forceps for removing foreign substance, a cleaning pipe, and an injection needle are projected from an opening at a distal tip of the hood to perform a treatment of a treatment object such as a lesion. Further, the hood having the distal tip formed in a tapered shape is easily inserted in pharynx, stomach, colon, duodenum, esophagus, and the like, making it possible to prevent a damage to the mucous membrane or the blood vessel. Further, this hood has a function of, for example, securing a good observation region by keeping a certain observation distance from the distal tip of the endoscope. Such a hood is tightly press-fitted in the distal tip of the insertion portion of the endoscope so as not to be easily detached when inserted in a human body.

Regarding this, there is known a technique in which a female screw portion is arranged on either one of an inner surface of the hood or an outer surface of the distal tip of the endoscope and a male screw portion screwed with the female screw portion is arranged on the other (Patent Literature 1). This technique can prevent the hood inserted in a human body from being easily detached.

CITATION LIST

Patent Literature

Patent Literature 1: JP 5404258 B2

SUMMARY OF INVENTION

Technical Problem

However, in the configuration in which the hood and the distal tip are screwed with each other, the hood can be mounted only to the endoscope having a female screw portion or a male screw portion arranged in the distal tip, limiting the use of the hood having a male screw portion or a female screw portion arranged therein. Further, in some endoscopes, for example, in a colonoscopy, a lubricant is applied to the insertion portion including the distal tip, and the hood to facilitate the insertion of the insertion portion of the endoscope into the large intestine. Thus, in the configuration in which the hood and the distal tip are screwed with each other, it is difficult to remove the hood to which the lubricant is adhered from the distal tip by pinching and rotating the hood. Further, an operator of the endoscope wears gloves on hands to prevent infection, and this makes it further difficult to remove the hood to which the lubricant is adhered. Further, it is also difficult to break the hood to which the lubricant is adhered for removing the hood from the distal tip.

Thus, a technique capable of easily removing the hood from the distal tip of the endoscope has been desired.

Thus, an object of the present invention is to provide a removal tool of a hood of an endoscope, having a structure capable of easily removing the hood that is fixed to a distal tip of the endoscope by press fitting from the distal tip of the endoscope, and a set of the hood and the hood removal tool.

Solution to Problem

An aspect of the present invention is a removal tool for removing a hood of an endoscope from a distal tip of the endoscope. The hood of the endoscope is mounted to an outer peripheral surface of the distal tip of the endoscope and has a hollow cylindrical shape, an outer surface of the hood is provided with a step portion that extends along a circumferential direction of the hood, and the removal tool is constituted from a flexible member provided with a hole-shaped recess capable of housing a part of the hood including the step portion inside the recess, and an inner wall surface of the recess is provided with an engaging portion at a position opposing to the step portion when the hood is housed in the recess, the engaging portion being shaped to grip the hood by being engaged with the step portion as a result of deformation of the flexible member.

An inner diameter of a part of the engaging portion arranged on the inner wall surface is preferably larger than an outer diameter of the step portion to prevent the engaging portion from being engaged with the step portion under anon-deformed condition of the flexible member.

Another aspect of the present invention is a set of a hood of an endoscope, the hood being mounted to an outer peripheral surface of a distal tip of the endoscope and having a hollow cylindrical shape, and a removal tool for removing the hood from the distal tip.

An outer surface of the hood is provided with a step portion that extends along a circumferential direction of the hood;

the removal tool is constituted from a flexible member provided with a hole-shaped recess capable of housing a part of the hood including the step portion inside the recess, and an inner wall surface of the recess is provided with an engaging portion at a position opposing to the step portion when the hood is housed in the recess, the engaging portion being shaped to grip the hood by being engaged with the step portion as a result of deformation of the flexible member.

An inner diameter of a part of the engaging portion arranged on the inner wall surface is preferably larger than an outer diameter of the step portion to prevent the engaging portion from being engaged with the step portion under a non-deformed condition of the flexible member.

The step portion is preferably arranged around an outer surface of the step portion, and the engaging portion is preferably arranged around the inner wall surface.

The outer surface of the hood is also preferably provided with a groove with both ends closed as the step portion, the groove extending along a circumferential direction of the hood; and the inner wall surface of the recess is also preferably provided with a projecting rib as the engaging portion, the projecting rib intermittently extending in a circumferential direction of the recess so as to correspond to the groove.

The removal tool is preferably a packing container that houses the hood, the packing container preferably include a housing chamber for housing the hood as the recess, and the engaging portion is preferably arranged on an inner wall surface surrounding the housing chamber of the packing container.

Further, it is also preferable that: the flexible member is an elastic member;

in the hood, the outer diameter of a part of the outer surface increases in a direction from the distal tip to the rear end on the opposite side, or, in the removal tool, the inner diameter of a part of the inner wall surface of the recess decreases in a direction from the inlet of the recess to the deep side, so that the inner diameter of the engaging portion is expanded as the engaging portion contacts the outer surface before the step portion reaches the position of the engaging portion while the hood is inserted into the recess from the distal tip of the hood; and when the step portion reaches the position of the engaging portion, the engaging portion and the step portion are engaged with each other by restoration of the engaging portion caused by elastic force generated by expansion deformation of the inner diameter of the engaging portion.

The hood preferably includes a main body portion having a cylindrical shape and a plurality of projecting elements projecting from the outer surface of the main body portion to a radial outer side in different directions; and the housing chamber of the packing container preferably include a columnar recess that houses the main body portion and a plurality of housing grooves projecting from the columnar recess to the radial outer side in different directions so as to correspond to the projecting elements, each of the housing grooves having a groove width and a groove depth capable of positioning and housing the corresponding projecting element.

At least in a part of the housing groove, a groove depth size of the housing groove is preferably larger than a thickness size of the corresponding projecting element.

The part where the groove depth size is preferably larger than the thickness size of the corresponding projecting element is configured to house at least a base of the projecting element that begins projecting from the main body portion.

The recess preferably includes a hole bottom, and a distance from the hole bottom to the engaging portion is equal to or longer than a distance from a distal tip of the hood to the step portion.

Advantageous Effects of Invention

According to the above hood removal tool of the endoscope and the set of the hood and the hood removal tool, the hood fixed to the distal tip of the endoscope by press fitting can be easily removed from the distal tip of the endoscope.

BRIEF DESCRIPTION OF DRAWINGS

FIGS. 7(a) to 7(e) each shows a diagram explaining the removal tool of the embodiment shown in FIG. 6 and removal of the hood from the distal-end rigid portion.

DESCRIPTION OF EMBODIMENTS

Figure 1:
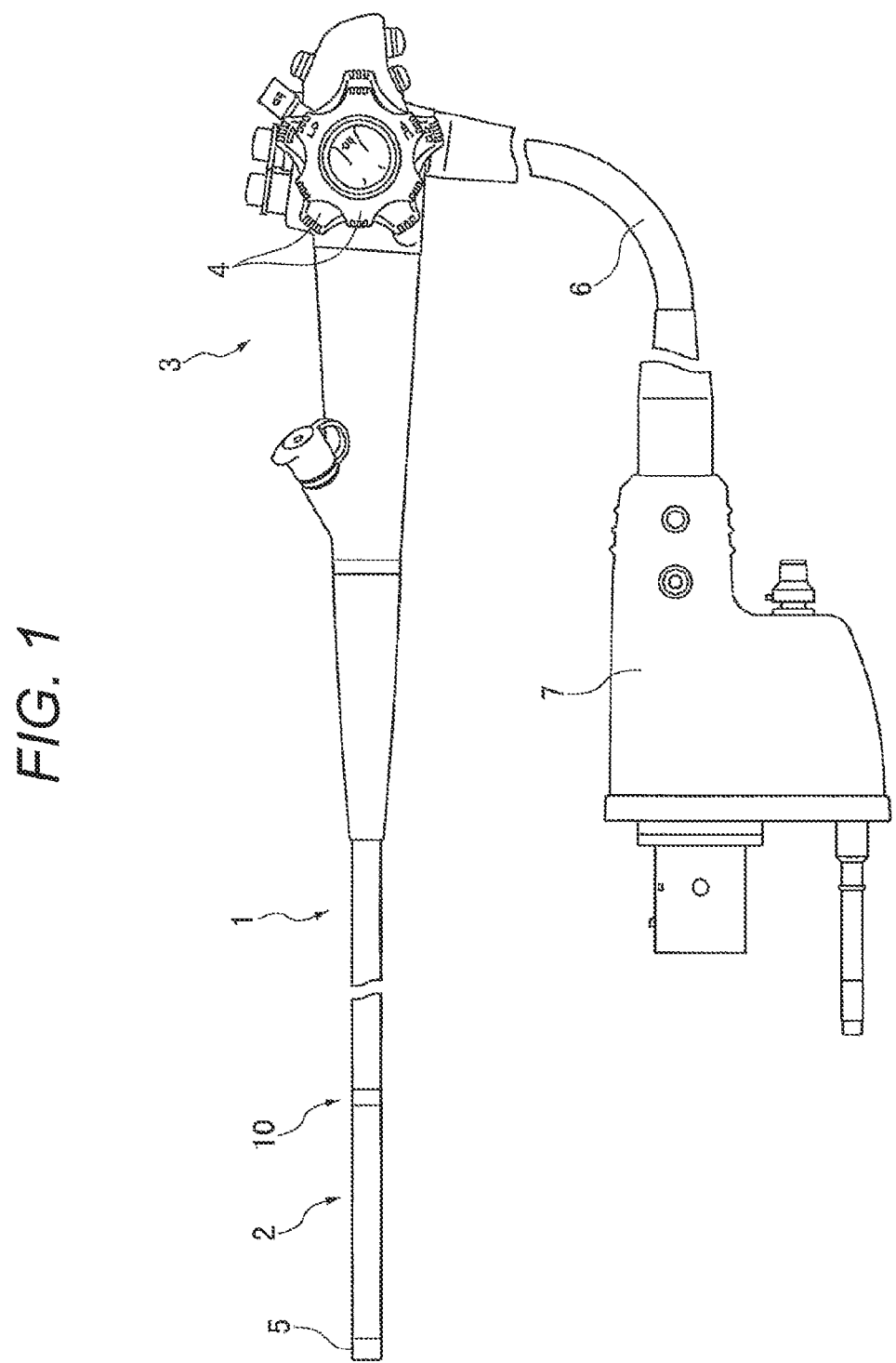
FIG. 1 shows an external perspective view of a medical endoscope of one embodiment.

Hereinafter, embodiments of the present invention will be described with reference to drawings. FIG. 1 shows an external perspective view of a medical endoscope of one embodiment. In the following description, regarding a forward/backward direction, the distal tip side of a flexible tube 1 of the endoscope is defined as "forward", and the distal tip side (side of a connector unit 7) of a universal tube 6 is defined as "backward".

A medical endoscope includes an operation unit 3, the flexible tube 1 extending forward from the operation unit 3 and having flexibility, a curved tube 2 connected to the front side of the flexible tube 1 via a connection portion 10, the universal tube 6 extending backward from the operation unit 3, and a connector unit 7 fixed to the rear end of the universal tube 6. A plurality of curved operation wires are inserted in the operation unit 3, the flexible tube 1, and the curved tube 2. A distal tip of each curved operation wire is connected to the rear end of a distal-end rigid portion 5, and a rear end of each curved operation wire is connected to a curved operation lever 4 (curved operation mechanism) of the operation unit 3. The curved tube 2 can be curved in a desired direction at a desired angle in accordance with an operation of the curved operation lever 4.

The distal tip of the curved tube 2 is provided with the distal-end rigid portion 5. The distal-end rigid portion 5 is constituted from a substantially elastically undeformable hard resin material (e.g., acrylonitrile butadiene styrene (ABS), modified polyphenylene oxide (modified PPO), polysulfone (PSU), etc.), and a distal tip face of the distal-end rigid portion 5 having a flat surface is provided with an opening equipped with an objective lens (observation lens), an outlet equipped with an illuminating lens, an air supply port/water supply port, a forceps port, and the like. The air supply port/water supply port is used to secure the visual field by expanding a body cavity of a patient through air supply. The air supply port/water supply port is also used, when observation performance of the endoscope is reduced due to the dirt on the objective lens surface caused by a body fluid or bleeding, to remove the dirt on the lens surface through water spraying and splash the water droplet on the objective lens surface through air blowing, thereby recovering the visual field. Further, the air supply port/water supply port is also used to acquire a clear observation image of a treatment object by blowing air to the surface of the treatment object. The forceps port is used to perform a biopsy or a treatment using various treatment tools and also to suck out a body fluid, the blood, the water sprayed from the air supply port/water supply port, and the like.

A light guide fiber (not illustrated) whose front end is connected to the illuminating lens is arranged inside the operation unit 3, the flexible tube 1, the curved tube 2, the universal tube 6, and the connector unit 7. Further, an image sensor (not illustrated) which is positioned right behind the objective lens is arranged inside the distal-end rigid portion 5, and an image signal cable extended from the image sensor is extended up to the inside of the connector unit 7 through the inside of the curved tube 2, the flexible tube 1, the operation unit 3, and the universal tube 6. The connector unit 7 is connected to a processor for an endoscope (not illustrated). The processor for the endoscope processes an image signal sent from the image sensor and perform control so as to display an image of an imaging object captured by the image sensor on a monitor (not illustrated).

Figure 2:
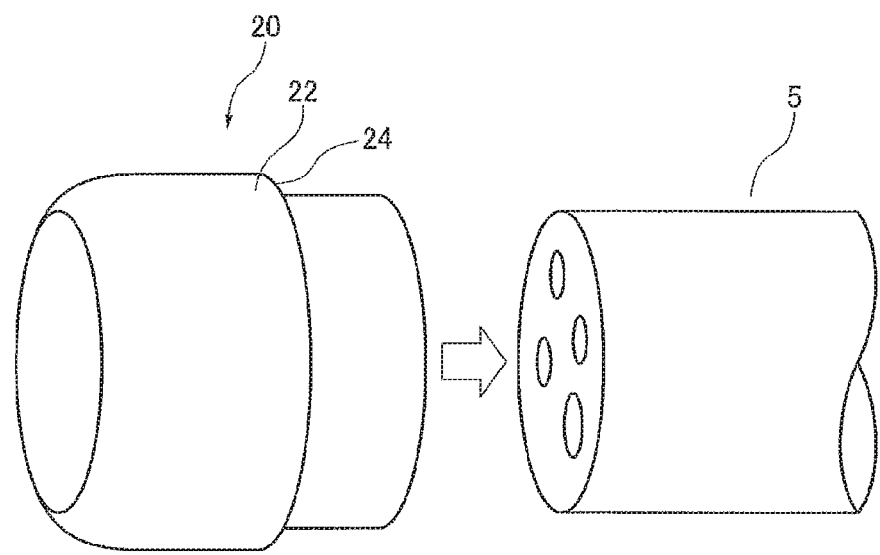
FIG. 2 shows a diagram explaining an endoscope hood of one embodiment.

FIG. 2 shows a diagram explaining an endoscope hood 20 of one embodiment. The hood 20 is tightly press-fitted in and mounted to the distal-end rigid portion 5 of the endoscope. The hood 20 can prevent the illuminating lens and the objective lens from becoming dirty with an adhered substance, facilitate the insertion of the endoscope into pharynx, stomach, colon, duodenum, esophagus, and the like, and prevent a damage to the mucous membrane and the blood vessel. Further, this hood has a function of securing a good observation region by keeping a certain observation distance from the distal-end rigid portion 5 of the endoscope.

The hood 20 has a hollow cylindrical shape and is mounted to the outer peripheral surface of the distal-end rigid portion 5 so as to project from the distal-end rigid portion 5. An outer surface 22 of the hood 20 is provided with a step portion 24 which extends along the circumferential direction of the hood 20. The hood 20 is formed from a resin material such as polyphenylene oxide and poly phenyl sulfone. The step portion 24 forms a step whose outer diameter decreases from the distal tip side to the rear side of the hood 20.

Such a hood 20 is tightly press-fitted in the distal-end rigid portion 5 so as not to be detached from the distal-end rigid portion 5 in a body cavity. Thus, as described above, it is sometimes difficult to remove the hood 20 after the endoscope is recovered from the body cavity. A lubricant is applied to the hood 20 for improving sliding performance of the endoscope in the body cavity, thus the lubricant is also adhered to the hood 20. This sometimes makes it difficult to remove the hood 20 from the distal-end rigid portion 5 by pinching the hood 20.

Thus, the present embodiment provides a removal tool 30 for removing the endoscope hood 20 from the distal-end rigid portion 5.

Figure 3:
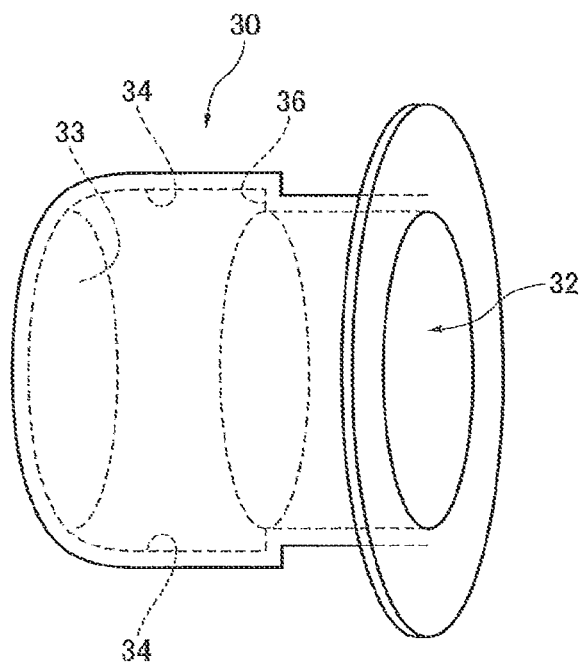
FIG. 3 shows an external perspective view of an example of a removal tool of one embodiment.

FIG. 3 shows an external perspective view of an example of the removal tool 30.

The removal tool 30 is constituted from a flexible member provided with a hole-shaped recess 32 which can house in its inside a part of the hood 20 including the step portion 24. The removal tool 30 includes a flat plate portion having a certain thickness around the recess 32. The recess 32 is recessed in a hole shape in a direction orthogonal to the plane of the flat plate portion. In one embodiment, the removal tool 30 is preferably a shell-shaped member. The recess 32 is a hole provided with a hole bottom 33. As shown in FIG. 3, an inner wall surface 34 of the recess 32 is provided with an engaging portion 36 which can be engaged with the step portion 24 of the hood 20 in a position opposing to the step portion 24 when the hood 20 is housed in the recess 32, for example, when the distal tip of the hood 20 is abutted to the hole bottom 33. The engaging portion 36 is shaped so as to grip the hood 20 by being engaged with the step portion 24 as a result of deformation of the flexible member of the removal tool 30 caused by an external force. In one embodiment, the shape of the engaging portion 36 is preferably a step shape corresponding to the step portion 24. In this case, the step shape has a large inner diameter on the deep side of the recess 32, but the inner diameter becomes smaller on the inlet side of the recess 32.

Note that, when the hood 20 is inserted inside the recess 32 such that the distal tip of the hood 20 mounted to the distal-end rigid portion 5 is abutted to the hole bottom 33, the step portion 24 does not need to be in a position completely opposing to the engaging portion 36, and the engaging portion 36 may be away from the step portion 24 on the inlet side of the hole. The engaging portion 36 is arranged such that the step portion 24 is opposed to the engaging portion 36 when the hood 20 is housed in the recess 32.

Note that the engaging portion 36 is engaged with the step portion 24 for gripping the hood 20 by virtue of deformation of the removal tool 30, thus the flexible member is preferably an elastic member. For example, the flexible member is constituted from an elastic resin material or the like.

Figure 4:
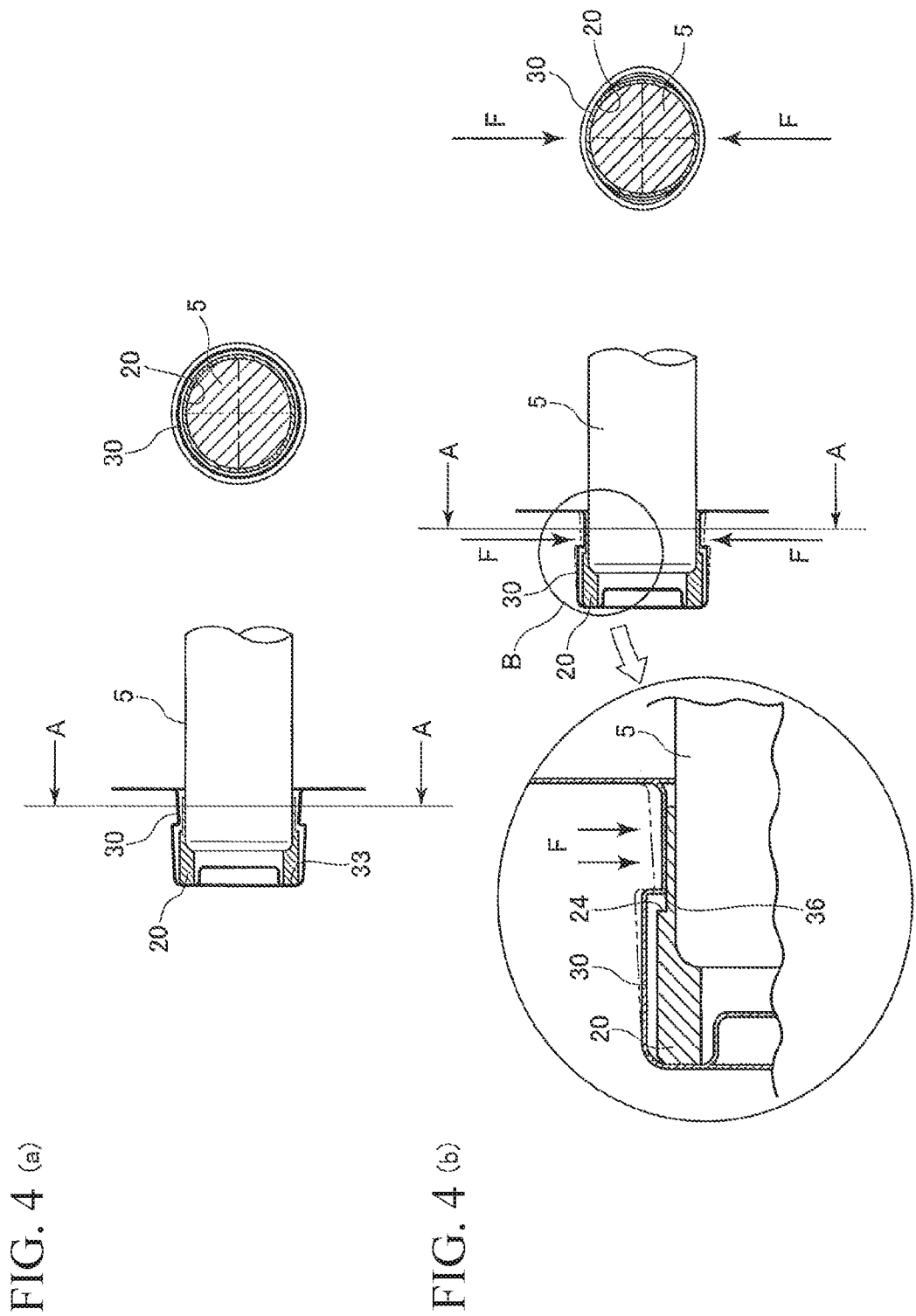
FIGS. 4(a) and 4(b) each shows a diagram explaining a configuration example of the removal tool and the hood of another embodiment.

FIGS. 4(a) and 4(b) each shows a diagram explaining an example of how to remove the hood of one embodiment using the hood removal tool.

FIG. 4(a) shows a state in which the hood 20 is inserted inside the recess 32 such that the distal tip of the hood 20 mounted to the distal-end rigid portion 5 is abutted to the hole bottom 33. In this state, the inner diameter of a part of the engaging portion 36 arranged on the inner wall surface 34 is preferably larger than the outer diameter of the step portion 24 to prevent the engaging portion 36 from being engaged with the step portion 24 under a non-deformed condition of the flexible member. Herein, the inner diameter of the part of the engaging portion 36 refers to the smallest inner diameter in a case where the engaging portion 36 forms a step, while the outer diameter of the step portion 24 refers to the largest outer diameter. In this configuration, the hood 20 can be inserted inside the recess 32 until the distal tip of the hood 20 mounted to the distal-end rigid portion 5 is abutted to the hole bottom 33 without encountering unnecessary resistance by the engaging portion 36. Thus, the inner diameter from the engaging portion 36 to the inlet of the recess 32 is also preferably larger than the outer diameter of the step portion 24. A cross section g an arrowed line A-A shown on the right side of FIG. 4(a) is obtained at a position closer to the inlet side of the recess 32 than the engaging portion 36. As shown in the figure, there is a gap between the outer surface of the hood 20 and the inner wall surface 34 of the recess 32.

FIG. 4(b) shows a state in which the distal tip of the hood 20 is abutted to the hole bottom 33 and the removal tool 30 is deformed. As shown in FIG. 4(b), when an external force F is applied to a part between the engaging portion 36 and the inlet of the recess 32 of the removal tool 30, for example, the external force F is applied from upper and lower directions in the figure by pinching this part with the fingers, the part described above is deformed as shown in FIG. 4(b) (refer to a cross section along an arrowed line A-A shown on the right side of FIG. 4(b)). By this deformation, the inner diameter of the engaging portion 36, positioned in the vicinity of the part described above, along the direction in which the external force F is applied becomes smaller. Thus, when the distal-end rigid portion 5 is taken out (pulled out) from the recess 32 in the deformed condition, the step portion 24 and the engaging portion 36 are engaged with each other and the hood 20 is gripped by the removal tool 30.

Thus, the hood 20 can be removed from the distal-end rigid portion 5 by taking out the distal-end rigid portion 5 from the recess 32.

In this configuration, the inner wall surface 34 of the recess 32 is provided with the engaging portion 36 shaped so as to grip the hood 20 by being engaged with the step portion 24 as a result of deformation of the inner wall surface 34 of the flexible member, thus the hood 20 can be easily removed from the distal-end rigid portion 5 by taking out the distal-end rigid portion 5 from the recess 32 while the hood 20 is being gripped even though a lubricant is adhered to the hood 20.

The embodiment shown in FIGS. 4(a) and 4(h) has a configuration in which the step portion 24 is provided around the outer surface of the hood 20 and the engaging portion 36 is provided around the circumference of the inner wall surface 34 of the removal tool 30. The configuration in which the step portion 24 and the engaging portion 36 are provided around the outer surface and the inner circumference, respective is preferable as the step portion 24 and the engaging portion 36 can be engaged with each other only by inserting the hood 20 in the recess 32 without being conscious of the peripheral positions of the step portion 24 and the engaging portion 36. However, in one embodiment, it is also preferable that the step portion 24 and the engaging portion 36 are intermittently arranged on the outer surface and on the inner circumference, respectively. In this case, for the step portion 24 and the engaging portion 36 to be engaged, the distal-end rigid portion 5 and the hood 20 are relatively rotated with respect to the removal tool 30 for the step portion 24 and the engaging portion 36 to be engaged.

Figure 5:
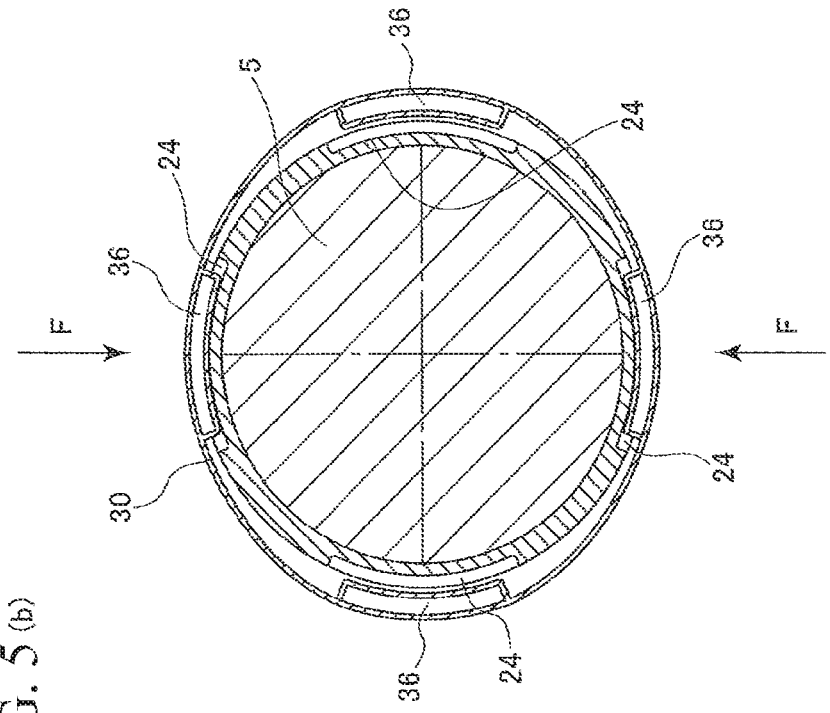
FIGS. 5(a) and 5(b) each shows a diagram explaining a configuration example of the removal tool and the hood of another embodiment.
Figure 5:
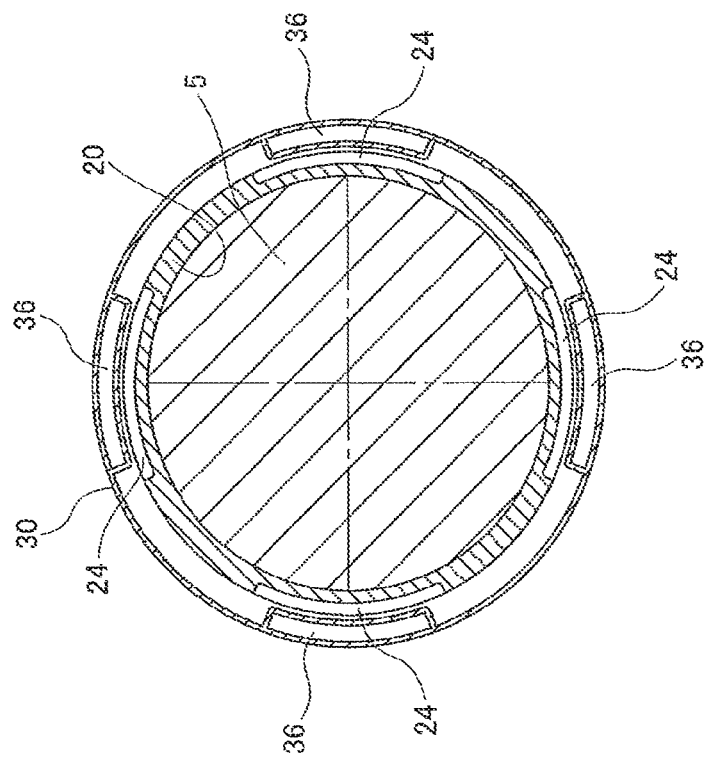

FIGS. 5(a) and 5(b) each shows a diagram explaining a configuration example of the removal tool 30 and the hood 20 of another embodiment. FIGS. 5(a) and 5(b) each shows a cross section of the removal tool 30, the hood 20, and the distal-end rigid portion 5 in a position where the step portion 24 and the engaging portion 36 are opposed to each other.

The outer surface of the hood 20 is provided with four step portions 24, each forming a groove with both ends closed, intermittently extending along the circumferential direction at a position having a certain distance from the distal tip of the outer surface of the hood 20.

Whereas, the inner wall surface 34 of the recess 32 of the removal tool 30 is provided with four engaging portions 36, each forming a projecting rib, intermittently extending in the circumferential direction, that is, extending by a predetermined length along the circumferential direction, so as to correspond to the grooves of the step portions 24.

Also in such an embodiment, as shown in FIG. 5(b), it is possible to grip the hood 20 inserted in the recess 32 by applying the external force F near the part where the step portion 24 is arranged to deform the engaging portion 36, thereby allowing the engaging portion 36 to engage with the step portion 24. Thus, the hood 20 can be easily removed from the distal-end rigid portion 5 by taking out the distal-end rigid portion 5 from the recess 32.

In this case, the length of the groove of the step portion 24 along the circumferential direction is preferably longer than the length of the projecting rib of the engaging portion 36 along the circumferential direction. For example, the length of the groove of the step portion 24 along the circumferential direction is preferably more than 100% but not more than 120% of the length of the projecting rib of the engaging portion 36. When one end of the projecting, rib of the engaging portion 36 is abutted to the closed end of the groove of the step portion 24, the distal-end rigid portion 5 can be pulled out from the recess 32 by relatively rotating the hood 20 and the distal-end rigid portion 5 with respect to the removal tool 30. This makes it possible to pull out the hood 20 from the distal-end rigid portion 5 by relatively rotating the hood 20 and the distal-end rigid portion 5 even if the hood 20 is tightly press-fitted into the distal-end rigid portion 5. The hood 20 can be easily removed from the distal-end rigid portion 5 like a cork of wine by rotating and pulling out.

FIGS. 6(a) to 6(d) and FIGS. 7(a) to 7(e) show diagrams explaining the removal tool 30 of yet another embodiment, mounting of the hood 20 to the distal-end rigid portion 5, and removal of the hood 20 from the distal-end rigid portion 5. FIGS. 6(a) to 6(d) explain an example of mounting the hood 20 to the distal-end rigid portion 5, while FIGS. 7(a) to 7(e) explain an example of removing the hood 20 from the distal-end rigid portion 5.

Figure 6:
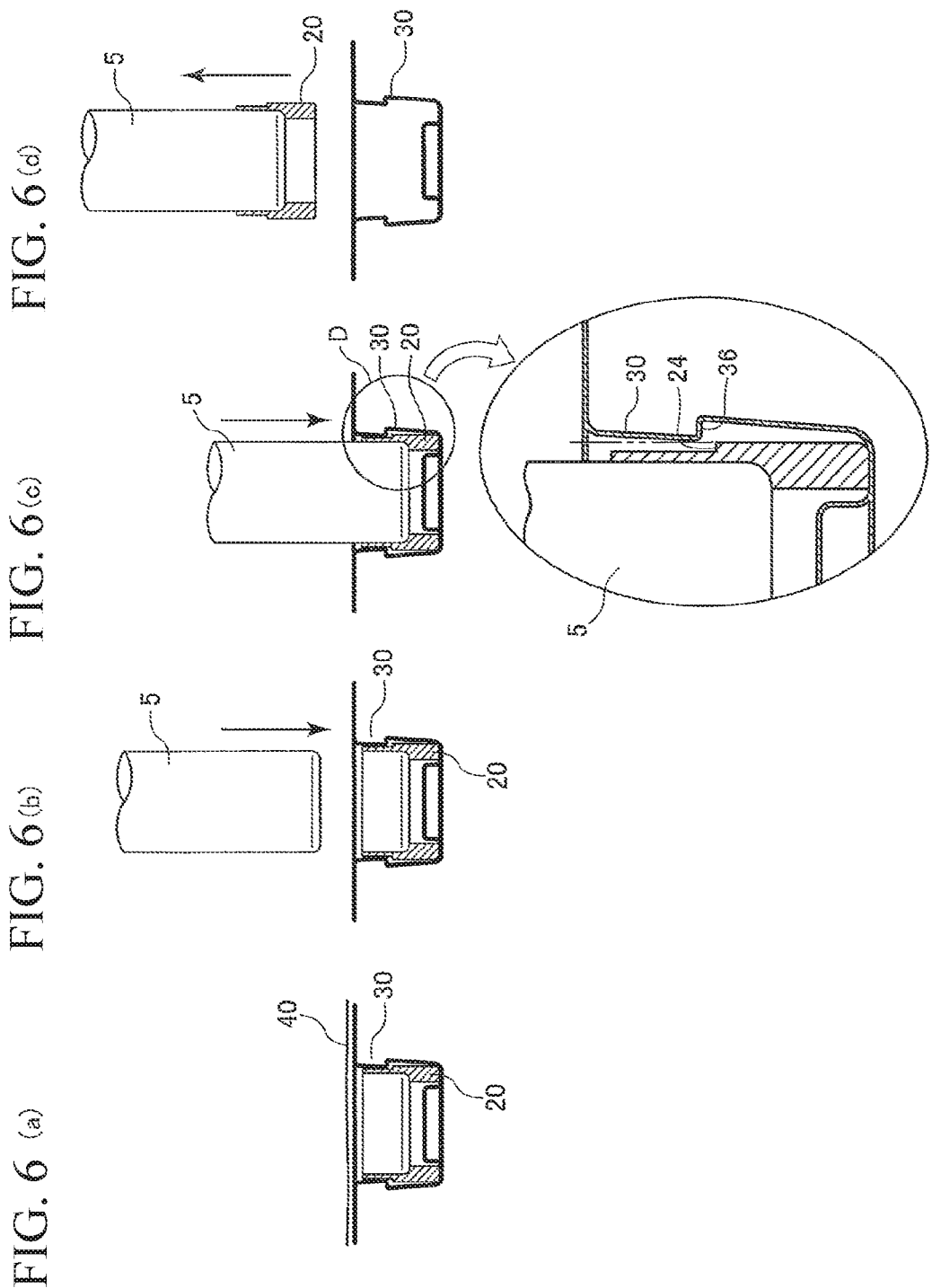
FIGS. 6(a) to 6(d) each shows a diagram explaining the removal tool of yet another embodiment and mounting of the hood to a distal-end rigid portion.

The removal tool 30 is a packing container that houses the hood 20. As shown in FIG. 6(a), a seal member 40 for sealing the hood 20 is stuck around the inlet of the hole of the recess 32 of the removal tool 30. Such a packing container is provided as a consumable. The inner wall surface 34 surrounding the recess 32 that serves as a housing chamber of the packing container s provided with the engaging portion 36.

When the hood 20 in the packing container is mounted to the distal-end rigid portion 5, the seal member 40 is peeled, and, as shown in FIGS. 6(b) and 6(c), the distal-end rigid portion 5 is inserted inside the recess 32 housing the hood 20 and pressed into the hood 20 having a cylindrical shape. Under a non-deformed condition of the flexible member of the removal tool 30, as shown in the enlarged view of a region D on the lower side of FIG. 6(c), the engaging portion 36 is not engaged with the step portion 24 as the inner diameter of the part of the engaging portion 36 arranged on the inner wall surface 34 is larger than the outer diameter of the step portion 24. As such, when the hood 20 that is press-fitted into the distal-end rigid portion 5 is taken out from the recess 32, as shown in FIG. 6(d), the distal-end rigid portion 5 to which the hood 20 is mounted can be taken out without being hooked to the engagement portion 36 as the step portion 24 is not engaged with the engaging portion 36 and there is a gap therebetween.

When the hood 20 is removed from the distal-end rigid portion 5 to which the hood 20 is mounted, as shown in FIGS. 7(a) and 7(b), the distal-end rigid portion 5 to which the hood 20 is mounted is inserted inside the recess 32 of the packing container and the distal tip of the hood 20 is abutted to the hole bottom 33 of the recess 32. At this point, as shown in FIG. 7(c), the external force F is applied to a part of the removal tool 30 on a side closer to the inlet than the position where the engaging portion 36 is arranged to cause deformation. By this deformation, the step portion 24 is engaged with the engaging portion 36, allowing the removal tool 30 to grip the hood 20. In this manner, as shown in FIG. 7(d), the distal-end rigid portion 5 is pulled out from the recess 32 under a state of applying the external force F, so that the hood 20 gripped by the removal tool 30 can be removed from the distal-end rigid portion 5, as shown in FIG. 7(e). According to one embodiment, it is preferable that the distance from the hole bottom 33 to the engaging portion 36 (e.g., the groove position or the step position of the engaging portion 36) is equal to or longer than the distance from the distal tip of the hood 20 to the step portion 24 (step position).

As described above, when the hood 20 is removed from the distal-end rigid portion 5, the step portion 24 is engaged with the engaging portion 36 and the hood 20 is gripped by the removal tool 30, thus the hood 20 can be easily removed from the distal-end rigid portion 5. Further, the hood 20 is not directly gripped by the fingers or through a glove, thus the lubricant can be prevented from adhering to the fingers or the glove.

Figure 8:
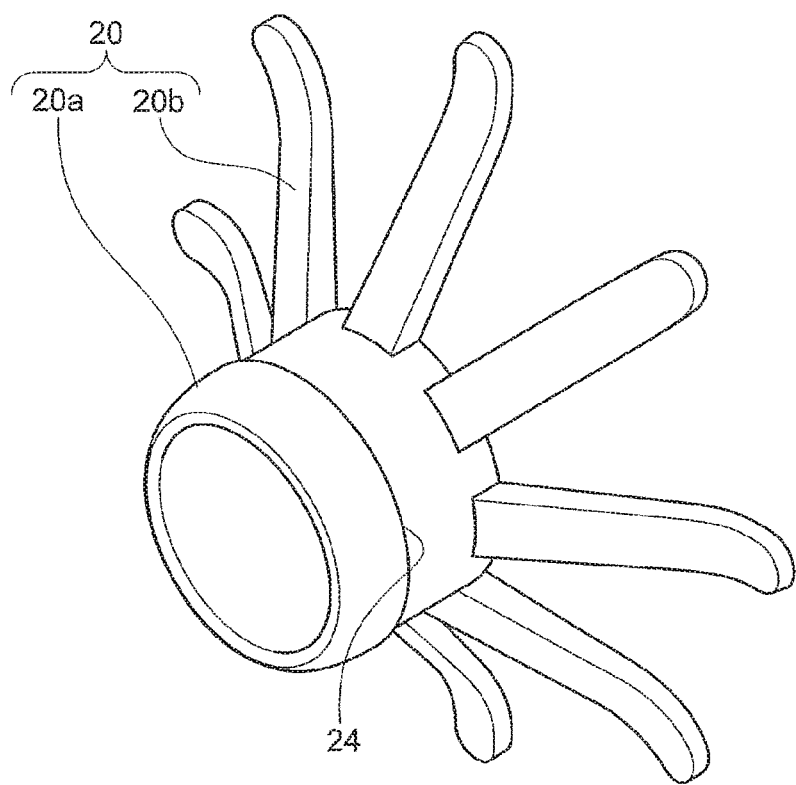
FIG. 8 shows a diagram explaining a shape of the hood of another embodiment.
Figure 9:
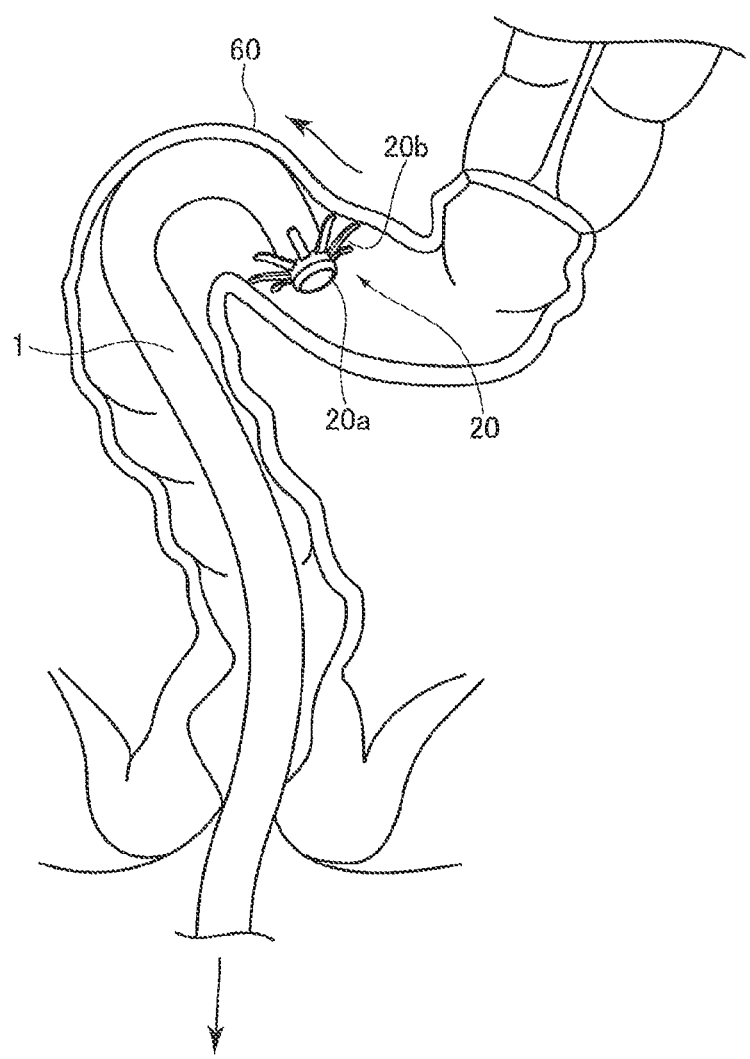
FIG. 9 shows a diagram explaining a method of using the hood of one embodiment.
Figure 10:
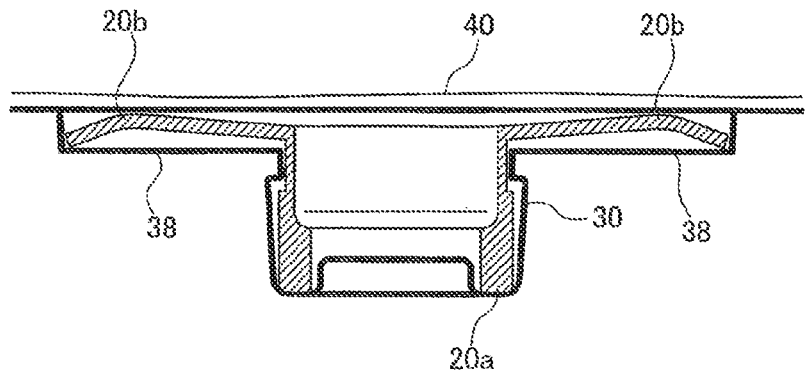
FIGS. 10(a) and 10(b) each shows a diagram explaining a packing container for housing projecting elements of the hood of one embodiment.
Figure 10:
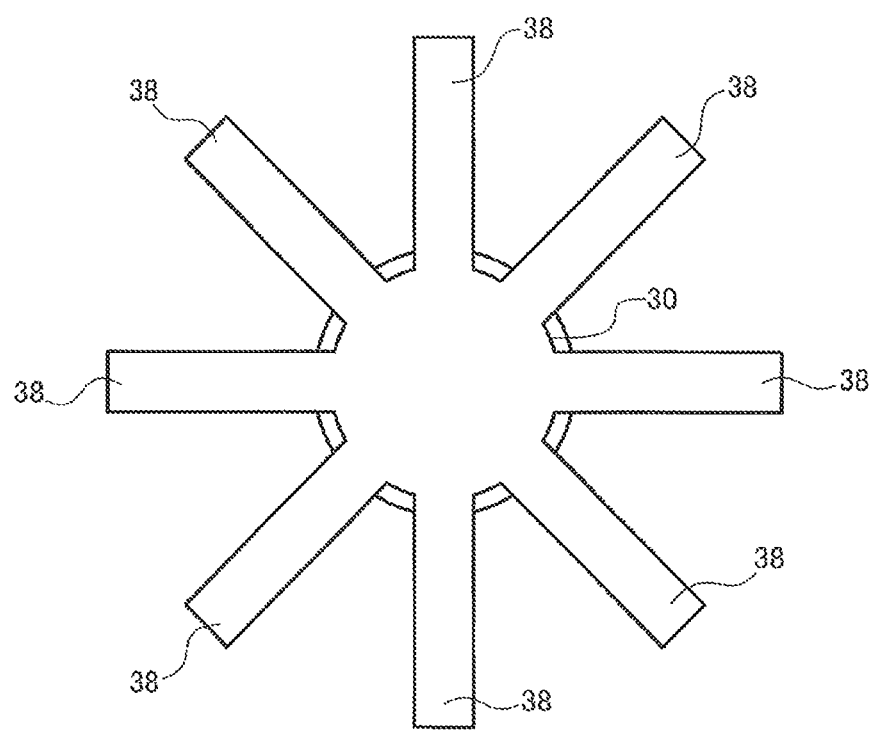

FIG. 8 shows a diagram explaining a shape of the hood 20 of one embodiment. FIG. 9 shows a diagram explaining a method of using the hood 20 of one embodiment. The hood 20 shown in FIG. 8 includes a main body portion 20a having a hollow cylindrical shape and a plurality of projecting elements 20b projecting from the outer surface of the main body portion 20a having a cylindrical shape to the radial outer side in different directions. In the hood 20, the projecting elements 20b are located on the rear end side of the step portion. When viewed from the distal tip of the distal-end rigid portion 5 to which the hood 20 is mounted, the rear end side is a side opposite to the distal tip. FIGS. 10(a) and 10(b) each shows a diagram explaining the packing container that houses the projecting elements 20b of the hood 20 of one embodiment.

As shown in FIG. 9, the endoscope in which such a hood 20 is mounted to the distal-end rigid portion 5 is inserted in a colon 60 and further in a body cavity such as the large intestine, and then a living tissue in the body cavity is observed while the endoscope is pulling out from the body cavity. In this operation, the large intestine or the like has a plurality of folds, thus, for closely examining the presence of a lesion by smoothing out the folds, the hood 20 is provided with the flexible projecting elements 20b capable of smoothing out the folds by contacting the surface of the biotissue. In the configuration where such a hood 20 is fixed to the distal-end rigid portion 5 of the endoscope by press fitting, in a case where a force acts on the hood 20 in the body cavity in a direction of detaching the hood 20 from the distal-end rigid portion 5, the hood 20 is more tightly press-fitted into the distal-end rigid portion 5 than the conventional case so as not to be detached from the distal-end rigid portion 5. According to one embodiment, when the distal-end rigid portion 5 is removed from the hood 20 by gripping the hood 20 with the removal tool 30, the gripping force of the removal tool 30 for gripping the hood 20 is required to withstand the pulling-out force for pulling out the distal-end rigid portion 5 without slipping, and the gripping force capable of withstanding the pulling-out force is preferably from 20 N to 100 N, particularly preferably from 50 to 100 N.

Further, according to one embodiment, in order to achieve the above gripping force, the shape size of the engaging portion 36 corresponding to the step portion 24, for example, the height size of the step of the engaging portion 36 shown in FIG. 3 and the groove depth size shown in FIGS. 5(a) and 5(b) are preferably 0.5 mm or more, more preferably 1.0 mm or more. The upper limit value of the step size and the groove depth size is limited due to the limitation of the deformation of the removal tool 30 caused by application of the external force F. According to one embodiment, the step size is preferably 5.0 mm or less, more preferably 3.0 mm or less.

Such a hood 20 is housed in the packing container which also serves as the removal tool 30 shown in FIGS. 10(a) and 10(b). Hereinafter, the packing container is represented by the same reference numeral 30 as the removal tool. As shown in FIGS. 10(a) and 10(b), a housing chamber of the packing container 30 includes a columnar recess for housing the main body portion 20a and a plurality of housing grooves 38 projecting from the columnar recess to the radial outer side in different directions so as to correspond to the projecting elements 20b, each of the housing grooves 38 having a groove width and a groove depth capable of positioning and housing the corresponding projecting element 20b. The housing grooves 38 are recessed in a groove shape from the plane of the flat plate portion surrounding the recess 32 of the packing container 30 (removal tool 30) in a direction orthogonal to this plane.

In an example shown in FIG. 10(a), the groove depth size of the housing groove 38 is larger than the thickness size of the corresponding projecting element 20b in any part. In this configuration, the hood 20 is arranged inside the packing container 30 so as to position the projecting elements 20b in the housing grooves 38, and the engaging portion is engaged with the step portion of the hood 20. When the hood 20 is pulled out from the distal-end rigid portion 5 in a such state, the relative movement of the packing container 30 along the rotation direction with respect to the hood 20 is prevented and the hood 20 can be efficiently pulled out with the large pulling-out force. When the hood 20 is pulled out from the distal-end rigid portion 5, in order to prevent the relative movement of the packing container 30 along the rotation direction with respect to the hood 20, the groove depth size of at least a part of the housing groove 38 may be made larger than the thickness size of the corresponding projecting element 20b. Also in this case, the part where the groove depth size of the housing groove 38 is larger than the thickness size of the corresponding projecting element 20b prevents the relative movement of the packing container 30 along the rotation direction with respect to the hood 20, thus the hood 20 can be efficiently pulled out with the large pulling-out force. For example, it is preferable that the part where the groove depth size of the housing groove 38 is larger than the thickness size of the corresponding projecting element 20b houses the base of the projecting element 20b that begins projecting from the main body portion 20a.

In the above embodiments, in order to prevent the engaging portion 36 from being engaged with the step portion 24 under a non-deformed condition of the removal tool 30, the inner diameter of the part of the engaging portion 36 arranged on the inner wall surface 34 is larger than the outer diameter of the step portion 24 and there is a gap therebetween as shown in FIG. 3(a) and FIG. 5(a). However, the configuration can be made such that, when the hood 20 is inserted in the recess 32 and the step portion 24 and the engaging portion 36 are opposed to each other, the step portion 24 and the engaging portion 36 are engaged with each other by the restoration of elastic deformation of the removal tool 30. According to one embodiment, the flexible member of the removal tool 30 is an elastic member, and, in the hood 20, the outer diameter of a part of the outer surface 22 gradually increases in a direction from the distal tip to the rear end on the opposite side, or, in the removal tool 30, the inner diameter of a part of the inner wall surface of the recess 32 decreases in a direction from the inlet of the recess 32 to the deep side, so that the inner diameter of the engaging portion 36 is expanded as the engaging portion 36 contacts the outer surface 22 of the hood 20 before the step portion 24 reaches the position of the engaging portion 36 while the hood 20 is inserted into the recess 32 from the distal tip thereof. It is preferable that, when the step portion 24 reaches the position of the engaging portion 36, the engaging portion 36 and the step portion 24 are engaged with each other by the restoration of the engaging portion 36 caused by the elastic force generated by expansion deformation of the inner diameter of the engaging portion 36. Also in this case, when the hood 20 is housed in the recess 32 and the engaging portion 36 reaches the position opposing to the step portion 24, the engaging portion 36 is automatically engaged with the step portion 24 by the restoring deformation of the elastic member and thereby can grip the hood 20, thus the hood 20 can be easily removed from the distal-end rigid portion 5 of the endoscope.

The removal tool of the hood of the endoscope of the present invention and the set of the hood and the hood removal tool have been described in detail above. It should be understood that the present invention is not limited to the embodiments described above and various changes and modifications may be made without departing from the scope of the present invention.

REFERENCE SIGNS LIST

1 Flexible tube
2 Curved tube
3 Operation unit
4 Curved operation lever
5 Distal-end rigid portion
6 Universal tube
7 Connector unit
10 Connection portion
20 Hood
20a Main body portion
20b Projecting element
22 Outer surface
24 Step portion
30 Removal tool
32 Recess
33 Hole bottom
34 Inner wall surface
36 Engaging portion
38 Housing groove
60 Colon

The invention claimed is:

1. A removal tool for removing a hood of an endoscope from a distal tip of the endoscope, the hood being mounted to an outer peripheral surface of the distal tip, the hood having a hollow cylindrical shape, an outer surface of the hood being provided with a step portion that extends along a circumferential direction of the hood, wherein:
the removal tool comprises a flexible member with a hole-shaped recess, the recess being capable of housing the step portion, and
an inner wall surface of the recess is provided with an engaging portion including a step where an inner diameter of the recess increases from a first diameter at an opening of the recess to a second diameter deeper in the recess, the step being provided at a position opposing to the step portion when the hood is housed in the recess, the engaging portion being configured to grip the hood by engaging with the step portion as a result of deformation of the flexible member, a flat plate portion is provided to surround the opening of the recess,
the recess is recessed to extend in a direction orthogonal to a plane of the flat plate portion, and
an outer diameter of the flat plate portion is greater than an outer diameter of the removal tool other than the flat plate portion.

2. The hood removal tool according to claim 1, wherein an inner diameter of a part of the engaging portion arranged on the inner wall surface is larger than an outer diameter of the step portion to prevent the engaging portion from being engaged with the step portion under a non-deformed condition of the flexible member.

3. The removal tool according to claim 1, wherein the removal tool has a tubular shape with the opening at one end of the removal tool in an axial direction of the tubular shape and a closed bottom at the other end of the removal tool in the axial direction,
an inner diameter of the recess closer to the closed bottom than the step is greater than an inner diameter of the recess closer to the opening than the step.

4. The removal tool according to claim 1, wherein the first diameter is a constant inner diameter from the opening of the recess to the step, and the constant inner diameter is smaller than an inner diameter of the recess farther from the opening than the step.

5. An endoscopic apparatus comprising:
a hood of an endoscope mounted to an outer peripheral surface of a distal tip of the endoscope, the hood having a hollow cylindrical shape and being provided with a step portion that extends along a circumferential direction of the hood; and
a removal tool configured to remove the hood from the distal tip, the removal tool comprising a flexible member with a hole-shaped recess, the recess being capable of housing the step portion;
wherein an inner wall surface of the recess is provided with includes an engaging portion including a step where an inner diameter of the recess increases from a first diameter at an opening of the recess to a second diameter deeper in, the recess, the step being provided at a position opposing to the step portion when the hood is housed in the recess, the engaging portion being configured to grip the hood by engaging with the step portion as a result of deformation of the flexible member.

6. The endoscopic apparatus according to claim 5, wherein an inner diameter of a part of the engaging portion arranged on the inner wall surface is larger than an outer diameter of the step portion to prevent the engaging portion from being engaged with the step portion under a non-deformed condition of the flexible member.

7. The endoscopic apparatus according to claim 5, wherein:
the step portion is arranged around an outer surface of the hood; and
the engaging portion is arranged around the inner wall surface.

8. The endoscopic apparatus according to claim 5, wherein:
the removal tool is a packing container that houses the hood;
the packing container includes a housing chamber for housing the hood as the recess; and
the engaging portion is arranged on an inner wall surface surrounding the housing chamber of the packing container.

9. The endoscopic apparatus according to claim 8, wherein:
the hood includes a main body portion having a cylindrical shape and a plurality of projecting elements projecting from an outer surface of the main body portion to a radial outer side in different directions; and
the housing chamber of the packing container includes a columnar recess that houses the main body portion and a plurality of housing grooves projecting from the columnar recess to the radial outer side in different directions so as to correspond to the projecting elements, each of the housing grooves having a groove width and a groove depth capable of positioning and housing the corresponding projecting element.

10. The endoscopic apparatus according to claim 9, wherein, at least in a part of the housing groove, a groove depth size of the housing groove is larger than a thickness size of the corresponding projecting element.

11. The endoscopic apparatus according to claim 10, wherein the part where the groove depth size is larger than the thickness size of the corresponding projecting element is configured to house at least a base of the projecting element that begins projecting from the main body portion.

12. The endoscopic apparatus according to claim 5, wherein:
the recess includes a hole bottom; and
a distance from the hole bottom to the engaging portion is equal to or longer than a distance from a distal tip of the hood to the step portion.

13. An endoscopic apparatus comprising
a hood of an endoscope mounted to an outer peripheral surface of a distal tip of the endoscope, the hood having a hollow cylindrical shape and being provided with a step portion that extends along a circumferential direction of the hood; and
a removal tool configured to remove the hood from the distal tip, the removal tool comprising a flexible member with a hole-shaped recess, the recess being capable of housing the step portion, wherein:

an outer surface of the hood is provided with a groove with both ends closed as the step portion, the groove extending along the circumferential direction of the hood; and an inner wall surface of the recess is provided with a projecting rib as an engaging portion, the projecting rib intermittently extending in a circumferential direction of the recess so as to correspond to and engage with the groove to grip the hood.

* * * * *